US005225260A

United States Patent [19]

McNaul et al.

[11] Patent Number: 5,225,260

[45] Date of Patent: Jul. 6, 1993

[54] SUBSURFACE PRINTABLE LAMINATE WITH CARRIER AND APPLICATION TAPE

[75] Inventors: Eric C. McNaul, New Berlin; Mary J. Janicek, Milwaukee; Brenda J. Anderson, Cedarburg, all of Wis.

[73] Assignee: Brady Coated Products Co., Milwaukee, Wis.

[21] Appl. No.: 676,618

[22] Filed: Mar. 28, 1991

[51] Int. Cl.⁵ .................... A61F 13/02

[52] U.S. Cl. .................... 428/40; 428/195; 428/211; 428/212; 428/213; 428/215; 428/219; 428/354; 428/421; 428/422; 428/914; 40/588; 40/589; 40/590; 40/615

[58] Field of Search .................... 428/40, 195, 211, 354, 428/914, 421, 422, 213, 215, 219, 220; 156/230, 247; 40/588, 589, 590, 615

[56] References Cited

U.S. PATENT DOCUMENTS

| | | | |
|---|---|---|---|
| 1,694,847 | 12/1928 | Donaldson | 428/203 |
| 1,702,663 | 2/1929 | Motter | 427/258 |
| 2,811,475 | 10/1957 | Edge | 428/914 |
| 3,133,854 | 5/1964 | Simms | 161/189 |
| 3,228,823 | 1/1966 | Usula et al. | 161/186 |
| 3,490,971 | 1/1970 | Walters | 428/40 |
| 3,616,192 | 10/1971 | Sinclair | 161/184 |
| 3,676,290 | 7/1972 | Hetrick | 161/189 |
| 3,734,807 | 5/1973 | Kelly | 161/5 |
| 3,967,022 | 6/1976 | Hasei | 428/40 |
| 4,020,204 | 4/1977 | Taylor | 428/40 |
| 4,049,479 | 9/1977 | Siker | 156/71 |
| 4,059,912 | 11/1977 | Noah | 428/40 |
| 4,068,028 | 1/1978 | Samonides | 428/40 |
| 4,125,653 | 11/1978 | Muzik | 428/40 |
| 4,211,809 | 7/1980 | Barta | 428/201 |
| 4,234,673 | 11/1980 | Scrutton | 156/230 |
| 4,421,816 | 12/1983 | Arnold | 428/202 |
| 4,514,457 | 4/1985 | Sasaki | 428/204 |
| 4,640,727 | 2/1987 | Janssen | 156/240 |
| 4,666,757 | 5/1987 | Helsinki | 428/203 |
| 4,678,690 | 7/1987 | Palmer et al. | 428/31 |
| 4,721,635 | 1/1988 | Helsinki | 428/15 |
| 4,855,171 | 8/1989 | McKie et al. | 428/43 |
| 4,902,363 | 2/1990 | Delaney | 156/230 |
| 4,927,709 | 5/1990 | Parker | 428/40 |

FOREIGN PATENT DOCUMENTS

| | | | |
|---|---|---|---|
| 661486 | 4/1963 | Canada . | |
| 0249109 | 5/1987 | Fed. Rep. of Germany . | |
| 61596 | 4/1982 | Japan | 428/914 |
| 557741 | 1/1975 | Switzerland . | |

OTHER PUBLICATIONS

Declaration of Eric C. McNaul (submitted Sep. 25, 1991).

*Primary Examiner*—Ellis P. Robinson
*Assistant Examiner*—Nasser Ahmad
*Attorney, Agent, or Firm*—Quarles & Brady

[57] ABSTRACT

Sheet material (20,20') including a polyvinyl fluoride film (21), an application tape (22) removably adhered to one surface (32) of the film (21) and a carrier tape (23) removably adhered to the application tape (22). The polyvinyl fluoride film (21) has an exposed surface (33) on which a sign (4) is printed in reverse image. Adhesive (42) is applied over the printed surface (33) with a transfer tape (40). When printed film (21) is applied to a selected surface, the film (21) is adhered to the selected surface by adhesive (42) after separation of the carrier tape (23) and application tape (22) so that the printed sign (4) is on the innermost surface (33) of the film (21) and protected by the thickness of the polyvinyl fluoride film (21).

13 Claims, 5 Drawing Sheets

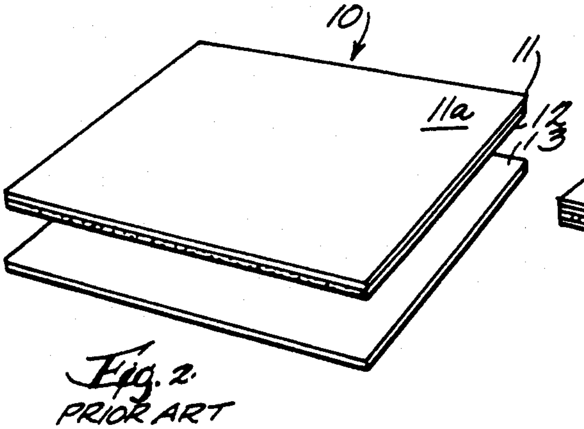
Fig. 2.
PRIOR ART
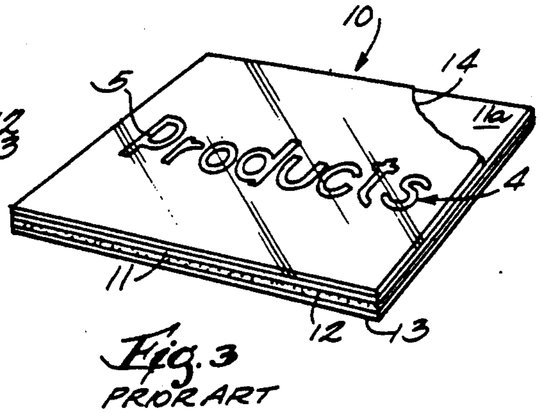
Fig. 3
PRIOR ART
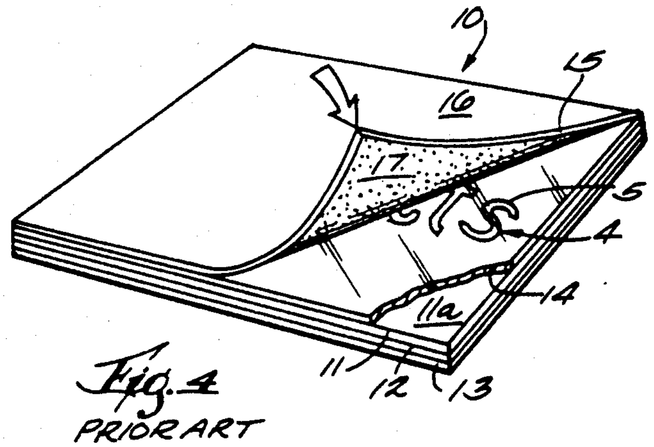
Fig. 4
PRIOR ART
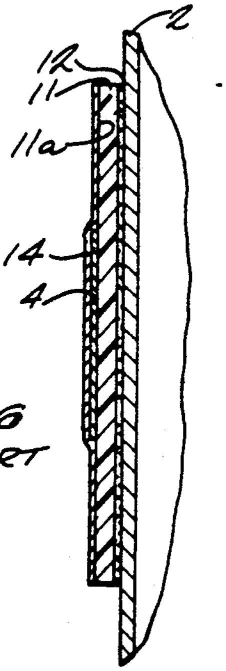
Fig. 6
PRIOR ART
Fig. 5
PRIOR ART
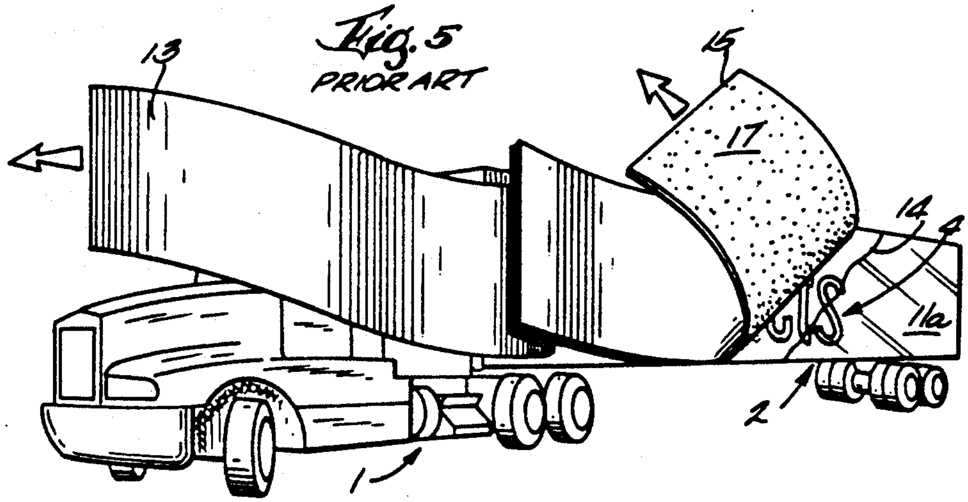

SUBSURFACE PRINTABLE LAMINATE WITH CARRIER AND APPLICATION TAPE

FIELD OF THE INVENTION

The present invention relates to the graphic arts field, more specifically to sheet material utilizing plastic films that can be printed with selected graphics and employed for outdoor signs.

BACKGROUND

Plastic films are currently used as substrates for outdoor signage in which graphics are printed on a film and the printed film is adhered to a surface with pressure sensitive adhesive. The graphics printed on the film typically include identification information, such as a company name or trademark, advertising, instructional information, product identification, decorative designs such as striping, etc. Some of the applications for outdoor signage of this type include printed panels on trucks and truck trailers, rental trailers, aircraft and other vehicles and, to a lesser extent, exterior architectural signage. Thus, major users of the type of outdoor signage material under consideration are owners and operators of fleets of trucks, trailers, vans, and airplanes. The printed graphics to be applied to an exterior surface can range in size from very small to very large, such as in the case of graphics that cover the side of a truck trailer. Delivery of printed outdoor graphics of this type to the end user typically involves several companies or entities between the manufacturer of the sheet material and the end user. The manufacturer produces an assembly of unprinted sheet material including an unprinted layer of plastic film that will be used for the final signage; the unprinted sheet material is purchased by a printing company that prints the end user's selected graphics on the film, overcoats the printed graphics with a clear coating if required, and laminates an application tape over the printed graphics; last, a company specializing in the application of graphics of the subject type will apply the printed films to the end user's equipment or buildings.

The prior art concerning sheet materials of the type to which this invention relates is described below in part 2 of the detailed description of this patent. One of the principal objectives of our invention is to provide a new construction for a sheet material assembly for use in producing printed exterior signage. Another principal objective of our present invention is to provide a new sheet material construction for printed outdoor signage that will provide the end user with enhanced performance as to weatherability and protection of the printed graphics. A further principal objective of our invention is to provide an assembly of sheet material to be printed with graphics for exterior signage that will facilitate and enhance the application of the printed film to a surface. These and other objectives of the invention will become apparent from the detailed description presented below with regard to the prior art, the new constructions of the present invention and comparison of our new sheet materials to those of the prior art.

SUMMARY OF THE INVENTION

Our present invention provides a subsurface printable sheet material for outdoor signage comprising (1) a polyvinyl fluoride film having a printable exterior surface, (2) an application tape comprising a substrate and a layer of pressure sensitive adhesive that is releasably adhered to an interior surface of the polyvinyl fluoride film opposite from the printable exterior surface thereof, and (3) a carrier tape including a substrate and a layer of pressure sensitive adhesive releasably adhered to a surface of the substrate of the application tape opposite from the adhesive layer thereof. When employed to provide a printed sign, the sign graphics are printed in reverse image on the exterior surface of the polyvinyl fluoride film of the sheet material, and the application tape and carrier tape remain joined to the film during the printing process. Thereafter, a layer of adhesive is applied over the printed surface of the polyvinyl fluoride film of the construction, such as by using transfer adhesive, and this adhesive is employed to affix the printed film to a selected surface. This provides a printed sign wherein the printed graphics are along the innermost surface of the polyvinyl fluoride film so that the graphics are covered by and protected by the film.

BRIEF DESCRIPTION OF THE DRAWINGS

A complete and enabling description of the present invention is set out below by reference to the following drawings, in which:

FIG. 2 is an exploded view of a typical prior art sheet material for outdoor printed signage;

FIG. 3 is a perspective view of the sheet material of FIG. 2 after being printed with a selected legend;

FIG. 4 is a perspective view of the printed material of FIG. 3 with an application tape added to the assembly;

FIG. 5 is a perspective view illustrating the manner in which the sheet material of FIGS. 2–4 is applied to a truck trailer body;

FIG. 6 is a vertical sectional view illustrating the final condition of the printed sheet material of FIGS. 2–4 after being applied to the truck body of FIG. 5;

DESCRIPTION OF PREFERRED EMBODIMENTS

1. Background, FIG. 1

Figure 1:
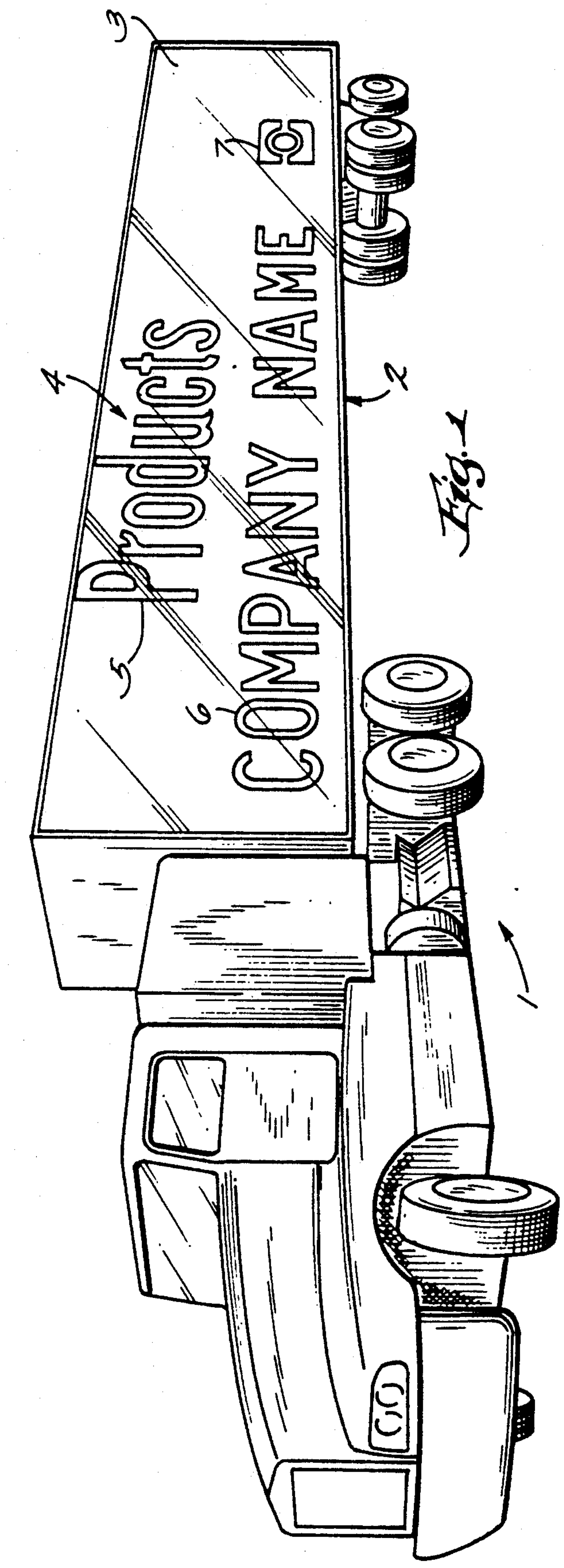
FIG. 1 is a perspective view illustrating a typical use of outdoor printed signage of the type to which the present invention relates.

A tractor trailer 1 is shown in FIG. 1 to illustrate one end use of the type of printed outdoor signage material to which the present invention relates. A side of the body of the trailer 2 is covered with a sign consisting of one or more panels of plastic film 3 on which a sign 4 has been printed. The exemplary sign 4 includes a legend 5 that identifies the product being shipped in the truck, a company name 6 and a trademark 7. The sign 4 can serve to provide product advertising and corporate identification, and signage of this type is a highly useful and informative media for many companies.

The opposite side of the trailer 2 also would have the same type of sign 4 applied to it, and in some instances the printed sign will appear on the front and back ends of the body of the trailer. The printed graphics typically will be in several colors and of a design to provide an attractive display. Although sign 4 shown in FIG. 1 is primarily intended as an advertising piece, signs of this type may instead, or in addition, include instructional information, or any other information or data selected by the end user. While a tractor trailer is illustrated in FIG. 1, many other types of over-the road vehicles also employ printed outdoor signage of this type, including fleets of vans. rental trailers and delivery vans; the printed graphics can be applied to automobiles for decorative purposes such as striping, as well as in the form of signs. Another significant use is on aircraft for identification or information signs or decorative applications. Printed plastic film of this type is also sometimes employed in architectural uses associated with buildings such as factories and commercial establishments.

Outdoor graphics of the type illustrated in FIG. 1 must be capable of withstanding exposure to difficult weather conditions, such as rain, snow and wide changes in temperature and humidity. Sunlight can cause fading of the printed graphics, so that the signage should show maximum UV stability in order to best serve the end user. Outdoor signage of this type is often plagued with graffiti that can be difficult to remove without damaging the printed graphics. Also, in the case of tractor trailers for example, repeated washing of the trucks to remove road grime presents another potential for damaging the outdoor signage. The application of a large sign such as sign 4 covering an entire side of a trailer is not an easy task, and a sheet construction that would facilitate application would be useful in this art.

2. Prior Art, FIGS. 2-6

FIGS. 2-6 illustrate a prior art construction of sheet material for outdoor printed graphics that now almost universally dominates the market in the absence of the availability of a superior material construction.

FIG. 2 illustrates sheet material 10 of the prior art that consists of a layer of vinyl film 11, pressure sensitive adhesive layer 12 along one surface of the vinyl film, and a release liner 13 covering the pressure sensitive adhesive. Vinyl film 11 typically is about 0.002" to 0.004" thick and most often is an opaque or translucent colored film, although there is limited use of transparent vinyl film for this layer. The liner is a sheet or web of relatively stiff paper, coated or impregnated with a suitable release coating, and supports film 11 during the printing of a sign. The surface of the layer of vinyl film 11 opposite from adhesive 12, indicated as surface 11*a* in the drawings, is exposed. Sheet material 10 comprises a first assembly for producing printed outdoor graphics of the form in which it is produced by the manufacturer and sent to a printing company.

The printing company applies the graphics selected by the end user to sheet material 10 by printing the selected graphics on exposed surface 11*a* of the layer of vinyl film 11. As illustrated in FIG. 3, a portion of sign 4, comprising the product legend 5, is printed on surface 11*a*. Surface 11*a* may be coated to provide good ink adhesion. Legend 5 is printed in normal left-to-right fashion as surface 11*a* of the prior art sheet material 10 will be the outermost, or exterior, surface of film 11 after application of the film onto a selected surface. After printed legend 5 has dried, surface 11*a* of film 11 is covered with a protective clear overcoating 14 which is necessary in order to protect the printed legend against degradation by UV radiation and physical damage by abrasion. Overcoating 14 may be formulated as a water based or a solvent based coating that must be oven-dried after application over surface 11*a* or a UV curable coating.

Turning now to FIG. 4, after the graphics have been printed on vinyl film 11, the next stage involves laminating an application tape 15 over the printed graphics. The application tape 15 in the prior art construction is a layer of paper 16 having a layer of low tack pressure sensitive adhesive 17 along its bottom surface. The low tack adhesive 17 is permanently bonded to the paper layer 16 to form the application tape so that the adhesive 17 will not separate from layer 16. The application tape is laminated to the printed sheet material of FIG. 3 by adhering its adhesive layer 17 over the overcoating 14 covering printed surface 11*a* of the sheet material. Application tape 15 typically is laminated to surface 11*a* bearing the printed graphics of FIG. 3 by the printing company after the printed graphics have been applied onto sheet material 10.

FIG. 5 represents the application of the printed assembly of FIG. 4 to trailer 2 of tractor trailer 1. The applicator company removes release liner 13 from the bottom of the sheet assembly and adheres the layer of pressure sensitive adhesive 12 on film layer 11 to the trailer body. Adhesive 12 is a tacky, high cohesive strength pressure sensitive adhesive that usually has some measure of repositionability for at least a limited period of time such as for about 20 minutes. The applicator company then removes application tape 15 from the assembly received from the printer, and the layer of low tack adhesive 17 releases from vinyl film 11 without physically damaging the film, coating 14 or removing the printed sign 4. The sign 4 after being adhered to trailer 2 is shown in sectional view in FIG. 6. The layer of pressure sensitive adhesive 12 on one surface of vinyl film 11 joins the sign to the trailer 2. Surface 11*a* of the vinyl film layer, which carries the printed sign 4 covered by overcoating 14, is the outermost surface of the film layer.

The prior art sheet material 10 as shown in the drawings and described above has several disadvantages. The vinyl film layer 11, which typically is a homopolymer of polyvinyl chloride or a copolymer comprising a major proportion of polyvinyl chloride with one or more comonomers, does not have good weather resistance and is particularly subject to deterioration upon exposure to ultraviolet rays from the sunlight. This problem is partially, but not completely, resolved by incorporating UV inhibitors or absorbers in the vinyl film. The printed sign 4 on the outer surface of the vinyl film when applied to the trailer is exposed to the elements and can be damaged by adverse weather conditions. Also, the sign is subject to damage by vandals, such as spray painting graffiti over the sign. These problems are to some extent resolved, but not completely adequately, by the use of various forms of clear overcoating, such as coating 14, that are applied after the sign has been printed and before it is adhered to a surface such as the trailer body. Also, in the prior art construction, the application tape 15 is a paper substrate that is opaque or nearly opaque. Even in view of, or in spite of, these and other shortcomings, sheet material 10 incorporating a layer of vinyl film is widely used for printable outdoor signage material and the market for this type of product is dominated by 3M, the Fasson Division of Avery International Corp. and Flexcon Company, Inc., with 3M being the principal supplier of the product. We have addressed the needs resulting from the inadequacies of the prior art sheet materials by developing the new sheet materials for outdoor printed signage described next in this specification.

3. First Embodiment of the Invention, FIGS. 7–15

A new sheet material assembly for outdoor printed signage and its application to trailer 2 is illustrated in FIGS. 7–15.

Figure 7:
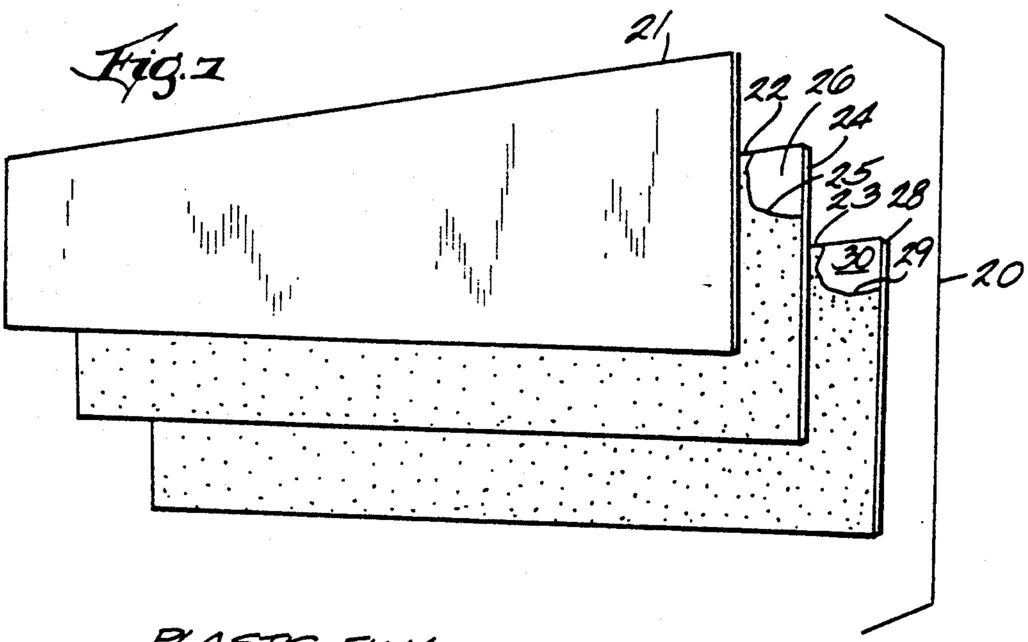
FIG. 7 is an exploded view illustrating the several layers of our new construction of adhesive sheet material for outdoor printed signage in accordance with the present invention.

Referring first to the exploded view of FIG. 7, sheet material 20 is a three-element composite structure consisting of plastic film 21, application tape 22 and carrier tape 23. Application tape 22 consists of a substrate 24 and a layer of low tack adhesive 25 on first surface 26 of the substrate. Carrier tape 23 consists of a substrate 28 and a layer of low tack adhesive 29 on first surface 30 of the substrate.

Figure 8:
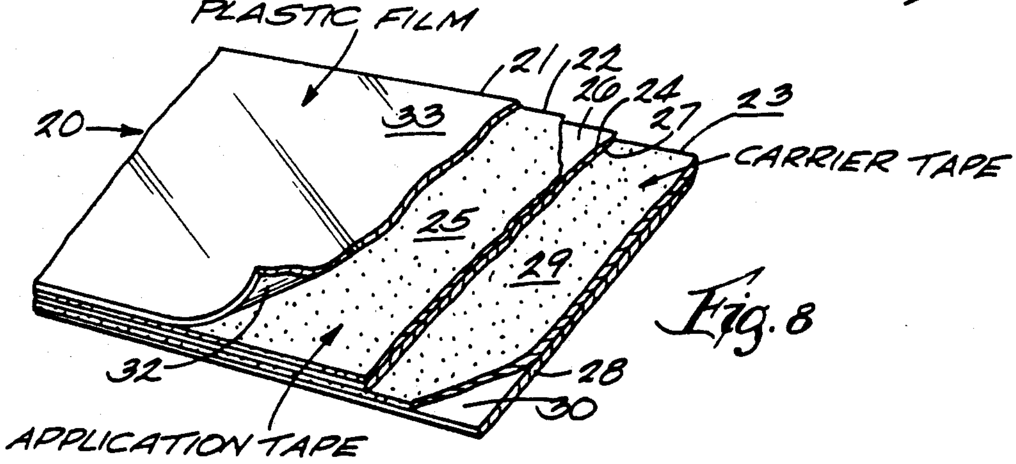
FIG. 8 is a perspective view, with portions broken away, of the layers of the sheet material of FIG. 7 joined together in a composite structure.

Film 21, application tape 22 and carrier tape 23 are joined together in a composite structure as shown in FIG. 8. Adhesive 25 of application tape 22 is releasably adhered to first surface 32 of film 21. Adhesive layer 29 of carrier tape 23 is releasably adhered to second surface 27 of the substrate of application tape 22, which is the surface thereof opposite from film 21. Film layer 21 has an exposed, or exterior, second surface 33.

Figure 9:
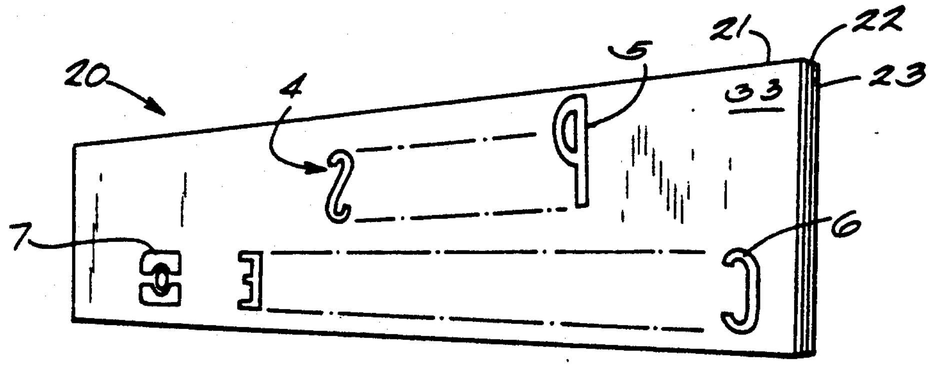
FIG. 9 illustrates the sheet material of FIG. 8 after being printed with a selected legend.

Sheet material 20 of the above structure is purchased by a printing company who will print an end user's sign on exposed surface 33 of the composite structure. FIG. 9 illustrates sign 4 printed on second surface 33 of the plastic film 21 of sheet material 20. (Note that several panels of sheet material 20 may be used for a large sign.) As indicated in the drawing, the elements 5–7 of sign 4 are to be printed in reverse image, for the reason which will become apparent below.

Figure 10:
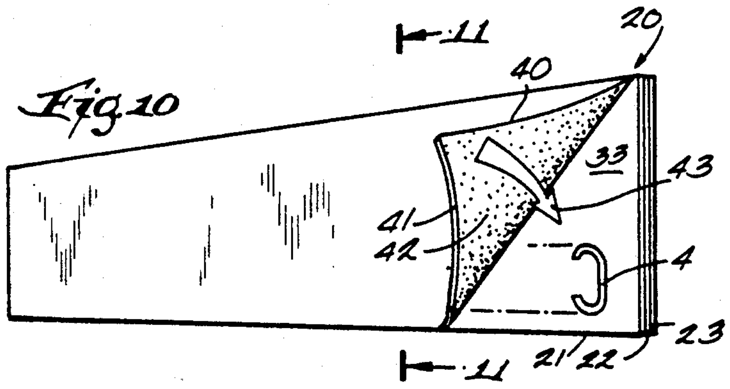
FIG. 10 illustrates the printed sheet material of FIG. 9 following a step subsequent to printing.

After sign 4 has been printed on surface 33 of one or more panels of sheet material 20, turning now to FIG. 10, the printer laminates a transfer tape 40 that has a layer of transfer adhesive over printed surface 33 of the sheet material. Transfer tape 40 includes a substrate 41 comprising a web of paper or plastic film impregnated or coated with a suitable release agent such as a silicone or carbamate coating and a layer of transfer adhesive 42 over one surface of substrate 41. Transfer adhesive 42 can be transparent or opaque; in the latter case, the adhesive can be pigmented to provide an additional color effect to the sign. Transfer tape 40 is joined to sheet material 20 with transfer adhesive layer 42 adhered to surface 33 of the plastic film, as indicated by arrow 43. The construction resulting after joinder of transfer tape 40 to sheet material 20 is shown in cross section in FIG. 11.

Figure 11:
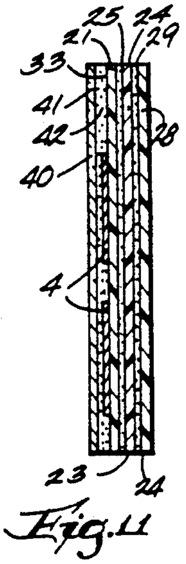
FIG. 11 is a sectional view of the sheet material illustrated in FIG. 10.
Figure 12:
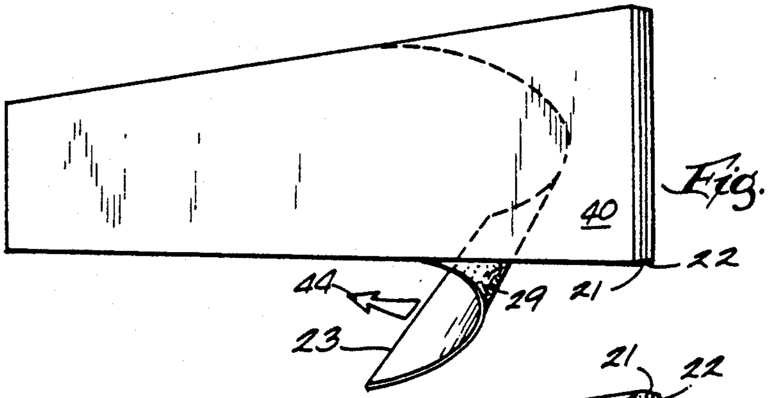
FIG. 12 is a perspective view illustrating the printed sheet material of FIGS. 7–11 during an initial step in the application thereof.

After transfer tape 40 has been joined to the sheet material, carrier tape 23 can be removed from the assembled product resulting from FIGS. 10 and 11. This is illustrated in FIG. 12, in which carrier tape 23 is shown as being removed from the assembly as indicated by arrow 44; low tack adhesive 29 on the carrier tape is releasably adhered to application tape 22 but strongly bonded to substrate 28 so that the adhesive will remain with the carrier tape during the removal operation. The operation illustrated in FIG. 12 may be performed by a printer after joining transfer tape 40 to the sheet material or can be carried out by an applicator company responsible for applying the sign to the selected surface of a vehicle or other object.

Figure 13:
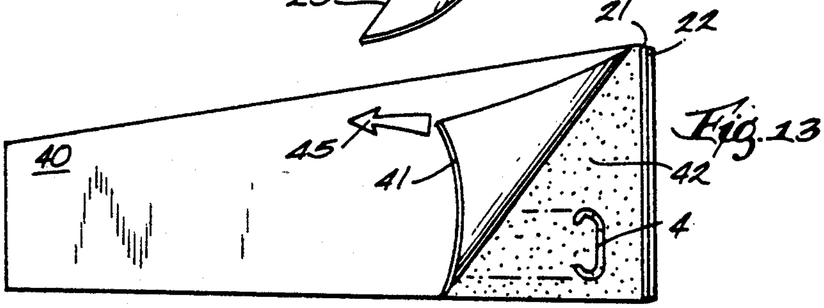
FIG. 13 is a perspective view illustrating the step of FIG. 12 from the opposite side of the printed sheet material.

FIG. 13 illustrates the first stage in the application of a sign made with sheet material 20 to a selected surface or object. The person applying the sign removes substrate 41 of transfer tape 40 from the assembled product, as shown by arrow 45; substrate 41 separates from adhesive 42 so that the layer of transfer adhesive 42 remains bonded to surface 33 of plastic film 21 of the sheet material 20. That is, adhesive 42 is transferred from transfer tape 40 onto film 21 after lamination of tape 40 to sheet material 20 and is exposed upon removal of the substrate 41 and forms the permanent adhesive that will be used to join the printed sign to an object.

Figure 14:
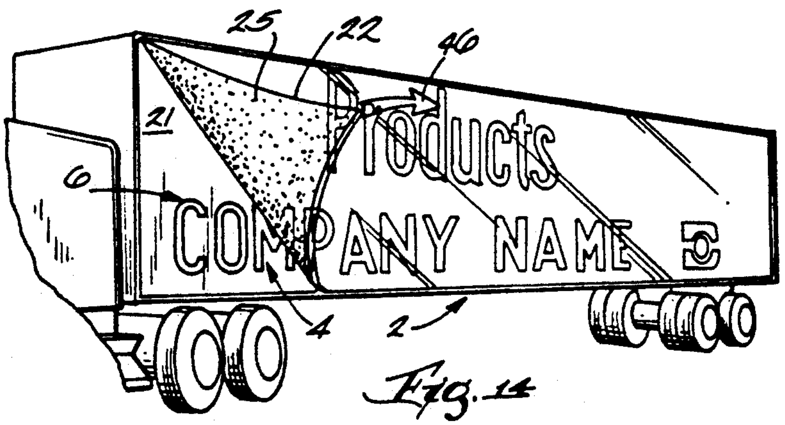
FIG. 14 is a perspective view illustrating the application of the printed sheet material of FIGS. 7–13 onto a trailer body.

As depicted in FIG. 14, the applicator adheres film 21 of sheet material 20 to the side of trailer 2 by pressing adhesive 42 onto the trailer. Either during application of film 21 or after it is fully adhered to the trailer, application tape 22 is peeled from film 21. Removal of the application tape is denoted by arrow 46. The layer of low tack adhesive 25 joining the application tape to film 21 is strongly bonded to substrate 24 of application tape 22 but releasably adhered to film 21 so that it separates from film 21 easily and without transfer of adhesive onto the film.

Figure 15:
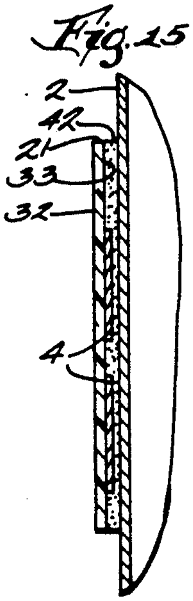
FIG. 15 is a vertical sectional view illustrating the printed sheet material of FIGS. 7–13 after application to the trailer body as shown in FIG. 14.

The completed application of a sign from film 21 of sheet material 20 is illustrated in cross section in FIG. 15. Film 21 is adhered to trailer body 2 by means of adhesive layer 42 which was transferred onto the film from transfer tape 40. Further, an important difference between the prior art construction of FIG. 6 and that of the new sheet material 20 is illustrated in FIG. 15 wherein it will be noted that second surface 33 of film 21 on which the sign 4 is printed is now on the innermost surface of film 21, next to adhesive 42, so that the printed sign is fully covered by film 21. First surface 32 of film 21 to which application tape 22 was releasably adhered is now the outermost surface of film 21.

Plastic film 21 of sheet material 20 described in this part 3 of the specification consists of a layer of polyvinyl fluoride film; suitable films are available commercially from E. I. du Pont de Nemours and Company Incorporated (Du Pont) under its registered trademark Tedlar ®. Film 21 may typically be in the range of 1 to 5 mils thick, preferably about 1 to 2 mils thick when it is to be applied on an uneven surface such as the side of a trailer body that may have rivets, ribs, etc. projecting from the body panels. A one mil thick film 21 of polyvinyl fluoride is especially useful since it provides an excellent conformable film for carrying and protecting the printed graphics at an economical cost. Film 21 is to be transparent (the term "transparent" as used in this specification and the claims with respect to film 21 and other film and adhesive layers is defined herein as including both transparent and translucent) because the sign 4 must be visible through the film after it is applied to an object such as trailer body 2 illustrated in the drawings. This enables the underlying color of the surface to which the film is applied to be visible through the unprinted areas of film 21, which can be useful in many installations. Also, however, if so desired, the printing company can apply a background color of printing ink around and behind the printed sign 4 after the sign is printed. This feature is advantageous in comparison to current commercial films for this type of signage that utilize colored films on which a sign is printed, which limits the end user to the colors available from the manufacturer of the sheet materials; however, with the present invention, background areas of surface 33 of film 21 can be printed in a broader palette of colors so as to thereby increase the choices available to the end user when selecting graphics for its trucks or other products. Surface 33 of film 21 on which the sign 4 is printed should be surface treated to enhance receptivity of the polyvinyl fluoride film to printing inks; any appropriate surface treatment technique can be employed, such as by activating surface 33 of the polyvinyl fluoride film by exposure to a gaseous mixture including a Lewis acid such as boron trifluoride, treating the surface with concentrated sulfuric acid or fuming sulfuric acid, flame treatment or high frequency corona discharge treatment. The various surface treatment systems form functional groups along surface 33, such as hydroxyl, carboxyl, carbonyl and ethylenically unsaturated radicals, that enhance the adhesion of printing ink to the surface. Polyvinyl fluoride film is available commercially from Du Pont that has one surface treated to increase ink receptivity or adhesion. Appropriately treated polyvinyl fluoride film can be printed with various types of commercially-available printing inks; we have tested and found suitable printing inks from several manufacturers, including the Sinvaqua® (water base) and Zephyrlon® (solvent base) series of inks sold by Sinclair and Valentine of N. Kansas City, Mo. the 9600 series of inks (solvent base) sold by KC Coatings Inc. of Lenexa, Kans., and the 11000 series of inks (solvent base) sold by T. W. Graphics Group of City of Commerce, Calif. Each of these series of inks is available in a wide range of standard colors from the manufacturers, and they also can be formulated in customized colors. Screen printing is the preferred technique for printing signs on the film 21 for most end uses. Further, film 21 when made of polyvinyl fluoride film may incorporate one or more ultraviolet light absorbing or screening compounds which act to screen selected wavelengths of ultraviolet radiation and thereby reduce UV degradation of the printed sign 4 and adhesive 42. Polyvinyl fluoride film incorporating ultraviolet light absorbers is available commercially from Du Pont.

Application tape 22 of sheet material 20 has a substrate 24 of transparent plastic film, which can be about 2 to 8 mils thick, preferably about 3 to 6 mils thick. Polyolefin films have been found to be particularly effective for the substrate of application tape 22; suitable films include low density polyethylene, medium density polyethylene, high density polyethylene, rubber modified high density polyethylene, polypropylene, and blends of polyethylenes. The plastic film employed for the substrate of application tape 22 should be very smooth as it is joined to film 21 during printing of a sign on exposed second surface 33 of film 21, and it is preferable that film 21 should not become embossed with any surface texture of the substrate of the application tape during the printing operation. We have found during our development work that a 0.003" thick substrate 24 of transparent rubber modified high density polyethylene is especially useful for the application tape when used with a 0.001" thick polyvinyl fluoride film layer 21. Adhesive 25 of the application tape can be any suitable adhesive that will exhibit the appropriate adhesion to film 21 and yet release cleanly therefrom when the application tape is to be removed from film 21 after the sign has been adhered to a selected surface such as the side of a trailer body. The term "releasably adhered" when used in this description and in the claims in connection with adhesive layer 25 (as well as other adhesive layers) is defined to mean that the adhesive releases from film 21 during application of the film without transfer of adhesive to the film 21. Thus, adhesive layer 25 is to release cleanly from film layer 21 and remain on the substrate 24 of the application tape when film 21 is affixed to a surface. Various low tack adhesives are appropriate for layer 25 such as low tack rubber based adhesives, acrylic adhesives, etc. An application tape 22 with an adhesive layer 25 of a type having adhesion to film 21 in the range of about 3 to 20 ounces per inch of width, preferably about 5 to 10 ounces per inch of width, is especially useful. Adhesive 25 also is transparent so that sign 4 printed on second surface 33 of film 21 is visible through the application tape as the sign is being applied. Further, the application tape, particularly the substrate 24 from which the tape is made, most usefully should have a low degree of shrinkage and minimum heat expansion; the latter characteristic is useful since the ink with which sign 4 is printed onto film layer 21 may be oven dried, air dried or UV cured and it is important that the application tape does not expand as it remains adhered to film 21 during the drying step.

The substrate 28 of carrier tape 23 may comprise a web or sheet of paper or plastic film. Suitable papers include polyethylene coated paper (coated on one side or two sides), clay coated papers, chrome coated papers, and densified kraft papers, most usefully with a basis weight in the range of about 90 to 150 pounds per ream of 3,000 square feet. A plastic film employed as substrate 28 of the carrier tape can be about 5 to 10 mils thick; a stiff plastic film such as high density polyethylene (e.g. 5 mils thick), polyester (e.g. 5–7 mils thick) or polyethylene terephthalate-glycol (e.g. 10 mils thick) or polystyrene (e.g. 10 mils thick) can be used. A specific material for substrate 28 of carrier tape 23 that has proved effective during our development work is two-side coated paper coated on one surface with low density polyethylene and coated on its opposite surface with high density polyethylene. The differential coating of the foregoing paper substrate for the carrier tape is employed so that the carrier tape will impart a slight degree of "back curl" to the sheet material 20 to counteract shrinkage of the application tape 22 and film 21 during drying of printing applied to the film so as to assist in maintaining the sheet material flat during drying. Substrate 28 of the carrier tape most usefully has initial back curl in the range of 4/32" to 12/32" measured at the corners of a 6 inch square of the substrate. Adhesive layer 29 of the carrier tape is applied to the surface of the foregoing paper substrate 28 that carries the low density polyethylene coating, and adhesive layer 29 is releasably adhered to second surface 27 of the substrate 24 of the application tape. With this arrangement, the surface of the substrate 28 with the high density polyethylene coating is a exterior surface of sheet material 20 and is slightly concave. Low tack adhesive layer 29 of the carrier tape may comprise an ultra removable pressure sensitive adhesive coated onto one surface of the substrate, or a slightly tacky film-forming coating.

As described above, transfer tape 40 is to include a layer of transfer adhesive 42 on substrate 41 that bonds to surface 33 of film 21 when the transfer tape is laminated to the printed surface. Various types of commercially-available adhesives can be used for transfer adhesive 42, including acrylic adhesives, which we presently prefer, rubber based adhesives, etc. The adhesive 42 is releasably adhered to substrate 41 of the transfer tape and exhibits higher bond strength to surface 33 of film 21 than its bond strength to substrate 41 after lamination, so that the adhesive will transfer to and remain bonded to surface 33 after removal of substrate 41. Adhesive 42 also should be a reasonably aggressive adhesive that will bond well to various surfaces, such as metal surfaces and plastic or fiberglass surfaces, so as to firmly hold a printed film 21 onto the selected surface to form a sign. We also prefer that the adhesive exhibit fairly low tack so that film 21 can be repositioned when applied to a surface to a sufficient extent to allow the printed film to be adjusted to a selected position on the surface.

4. Second Embodiment of the Invention, FIGS. 16 and 17

Figure 16:
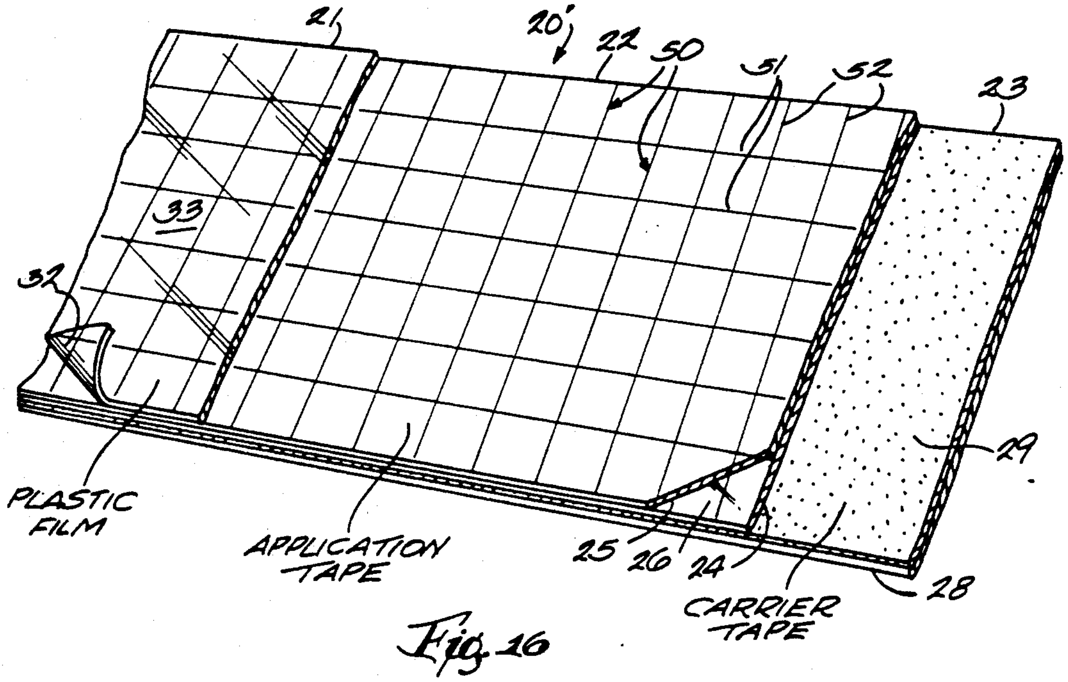
FIG. 16 is a perspective view, with portions broken away, of a second new sheet material construction according to the present invention.
Figure 17:
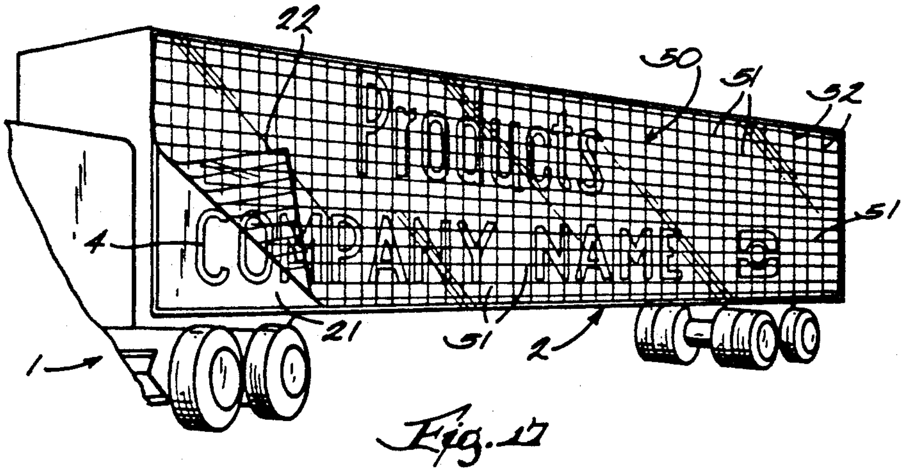
FIG. 17 is a side view, with portions broken away, illustrating application of a sign printed on the sheet material of FIG. 16 onto a truck trailer body.

FIGS. 16 and 17 illustrate a second subsurface printable sheet material assembly for outdoor printed signage according to the present invention, identified as sheet material 20'.

Sheet material 20' includes all of the same elements as sheet material 20 described above in part 3, which are identified by the same reference numerals in FIGS. 16 and 17. Sheet material 20' consists of plastic film 21 of polyvinyl fluoride film, application tape 22 including substrate 24 and adhesive 25, and carrier tape 23 including substrate 28 and adhesive 29. Substrate 24 of application tape 22 is a layer of transparent plastic film, as in sheet material 20. The several elements of sheet material 20' are joined together in the same manner and arrangement as in sheet material 20.

The new structure of sheet material 20' as compared to sheet material 20 resides in reference line means which are formed, as by printing, on one of the surfaces of substrate 24 of the application tape. The reference line means is indicated by the general reference numeral 50 in FIG. 16. In the exemplary embodiment, reference line means 50 comprises a series of spaced parallel horizontal lines 51 and a series of spaced parallel vertical lines 52 arranged to intersect a right angles to each other. Other line constructions may be used for the reference line means 50; for example, the reference line means can comprise only one set of lines rather than the grid shown in the drawings, such as one set of spaced parallel horizontal lines or one set of spaced vertical lines, or one or more sets of lines arranged at different angles than as shown in FIG. 16. Lines 51 and 52 may be applied to either surface of substrate 24 of the application tape. The spacing between lines 51 and the spacing between lines 52 can vary within a broad range. For example, our development work to date indicates that spacing in the range of one inch between the lines to six inches between the lines is especially useful for the intended purpose, although even wider spacing can be used if so desired. A grid of parallel horizontal lines 51 that are one inch apart and parallel vertical lines 52 that are one inch apart represents our best mode for practicing this embodiment of our invention at the time of filing this patent.

After sign 4 is printed on surface 33 of film 21, transfer tape 40 is applied over printed surface 33 of sheet material 20' in the same manner illustrated in FIG. 10. Next, carrier tape 23 is removed from sheet material 20' in the same manner as illustrated in FIG. 12. When the sign printed on sheet material 20' is ready to be applied to an object, substrate 41 of transfer tape 40 is removed from the assembly in the manner illustrated in FIG. 13 and as previously described, which results in adhesive 42 of the transfer tape remaining bonded over surface 33 of sheet material 20'.

The application of a sign printed on sheet material 20' is illustrated in FIG. 17. At this stage of the process, the assembly includes film 21 with sign 4 printed along its second surface 33, transfer adhesive layer 42 over the printed second surface 33 and application tape 22 releasably adhered to the opposite first surface 32 of film 21. Inasmuch as substrate 24 of the application tape and film 21 are transparent, both the printed sign 4 on innermost surface 33 of film 21 and the lines 51 and 52 printed on substrate 24 of application tape 22 are visible to the person applying the sign. The lines 51 and 52 are employed to obtain appropriate alignment of the printed sign on trailer 2 as the person applying the sign can use them as reference lines as an aid in obtaining the appropriate registration or arrangement of the sign on the trailer. The reference line means exemplified by lines 51 and 52 thereby assists in obtaining accurate placement of the sign graphics printed on film 21 on the object to which the sign is to be adhered. The final configuration of a sign applied to trailer 2 with sheet material 20' is the same as shown in FIG. 15.

5. Third Embodiment of the Invention

A third subsurface printable sheet material for outdoor printed signage according to our present invention involves using a different substrate 24 for the application tape 22 of sheet material 20 and/or sheet material 20', all other structure being the same as illustrated in FIGS. 7 and 8. Instead of substrate 24 of transparent plastic film as described in parts 3 and 4 of this specification, the substrate 24 can be a layer of opaque or nearly opaque plastic film or paper. An opaque plastic film for substrate 24 can have the same characteristics as described for the substrate in part 3 of this specification. Paper when used for substrate 24 should be slightly stretchy so as to preclude problems when printing a sign on film 21 and to facilitate application of the sign. Also, a paper substrate 24 should have a smooth first surface so that film 21 does not become embossed with any surface texture of the paper substrate.

The printing and subsequent application of a sign with sheet material of this embodiment is the same as described in part 3 and illustrated in FIGS. 9–15. Sheet material made with a paper or opaque plastic film as the substrate of the application tape provides a signage material having the advantages described in parts 3 and 4 above, except that the printed sign may not be clearly visible during application because of the opaqueness of the application tape substrate. This may be suitable in various uses of the sheet material, inasmuch as persons who apply signs of this general type are presently accustomed to using a paper application tape. Printed reference line means on an opaque substrate can be useful in obtaining proper alignment of the printed sign on the object or surface to which it is applied.

The following Examples 1-3 describe three specific constructions of subsurface printable sheet material assemblies according to our present invention which have been tested in the field (Examples 1 and 2) or under laboratory conditions (Example 3) as of the filing date of this patent. Various physical properties of the several layers of the constructions as set forth in the Examples were measured according to appropriate procedures of the American Society for Testing Materials (ASTM) or Pressure Sensitive Tape Council (PSTC) as follows: thickness, PSTC-33; tensile strength, PSTC-31, using an Instron ® machine operated at a crosshead speed of 5 mm/minute except as otherwise noted; burst strength, ASTM D-774 Elmendorf tear strength, PSTC-38; stiffness, PSTC-37; adhesion, PSTC-4 except that adhesion of the transfer adhesive layer was measured according to PSTC-1; Kiel release value, PSTC-4; and polyken probe tack, ASTM D-2979. A "ream" as used in the Examples in connection with basis weight means 3,000 square feet of material, either plastic film or paper. The "machine direction" of a web of material is identified as MD and "cross machine direction" as XD in the Examples.

Several other physical properties were measured according to test procedures which we devised. Shrinkage of some of the materials used in the Examples was determined by very accurately marking off a 6"×6" square of a larger piece of the selected material, and measuring the exact length of all four sides to four decimal places. The sample was then placed in a preheated oven at a selected temperature for 20 minutes on a flat glass plate. The sample was removed from the oven and allowed to sit at room temperature for 30 minutes, following which the four sides of the square were again accurately measured. The percentage of shrinkage was calculated by comparing the change in area of the square of material. The curl of the carrier tape described in the Examples was measured by cutting a 6"×6" square of the material, and measuring the curl at each corner of the sample in 1/32 inch increments. The sample was placed on a flat countertop, and the curl measured as the distance between the countertop and each of the four corners of the sample; the initial back curl was then taken as the average of the four measurements.

EXAMPLE 1

Sheet material 20' as described in part 4 above and illustrated in FIGS. 16 and 17 was made as follows.

Plastic Film 21: a layer of 0.001" thick transparent polyvinyl fluoride film available commercially from Du Pont under its designation Tedlar ® TUT10AG3FHA, which is a heat stabilized polyvinyl fluoride film having one surface, second surface 33, treated for ink receptivity and its opposite first surface 32 untreated. The film incorporated ultraviolet absorbers and had a UV transmission of less than 0.2% between 190 nm and 350 nm. The film had a basis weight of 22 pounds/ream and the shrinkage of a 6"×6" square of the film was 0.07% at 150° F. The tensile strength of the film when elongated to 5% was 5.7 kg/inch width (MD) and 5.4 kg/inch (XD) at 30° F., 2.4 kg/inch width (MD) and 2.4 kg/inch width (XD) at 75° F., and 1.7 kg/inch width (MD) and 1.5 kg/inch width (XD) at 110° F.

Application tape 22: a substrate 24 of 0.003" thick transparent rubber modified high density polyethylene film with a 0.0005" thick adhesive layer 25 consisting of transparent acrylic adhesive on first surface 26 of the substrate. The total basis weight was 44 pounds/ream. When elongated to 5%, the application tape had a tensile strength of 5 kg/inch width (MD) and 5.4 kg/inch width (XD) at 30° F., 1.5 kg/inch width (MD) and 1.8 kg/inch width (XD) at 75° F., and 1.5 kg/inch width (MD) and 1.8 kg/inch width at 110° F. The shrinkage of a 6"×6" square of the application tape was 0.33%. First surface 26 of substrate 24 of the application tape was printed with a grid of MD parallel lines spaced 1" apart and XD parallel lines spaced 1" apart to provide reference lines 51 and 52, respectively, as illustrated in FIGS. 16 and 17.

Carrier Tape 23: a substrate 28 of natural machine finish paper with a basis weight of 90 pounds/ream coated on one surface with 14 pounds/ream of low density polyethylene (LDPE) and coated on its opposite surface with 14 pounds/ream of high density polyethylene (HDPE). The coated substrate had a basis weight of 118 pounds/ream, was 0.0091" thick and had a minimum tensile strength (measured with crosshead speed of 10 mm/minute) at break of 35 kg/inch width (MD) and 15 kg/inch width (XD) with nominal elongation of 2% (MD) and 3.4% (XD), and stiffness of 11.3 Taber units (MD) and 24.7 Taber units (XD). The initial back curl of a 6"×6" square of the coated substrate was 9/32". A nonaggressive, low tack modified rubber based adhesive was coated over the LDPE coating of the substrate at a weight of 15 pounds/ream to form adhesive layer 29 of the carrier tape.

The sheet material 20' of this Example 1 was assembled by adhering the above application tape 22 to first surface 32 of the polyvinyl fluoride plastic film 21; the adhesion of adhesive layer 25 of the application tape 22 to the first surface 32 of film 21 was 5 ounces/inch of width, so that the adhesive layer was "releasably adhered" to surface 32 of the film 21. Next, the adhesive layer 29 of the above carrier tape 23 was adhered to second surface 27 of the substrate of the application tape 22; the adhesion of the adhesive layer 29 to second surface 27 of the substrate of the application tape was measured at 14 ounces/inch of width so that adhesive layer 29 was releasably adhered to the second surface. The exposed second surface 33 of film 21, which is an exterior surface of sheet material 20', was screen printed with several test signs including numbers and design elements in from one to four colors. The inks used for printing the signs were the Zephyrlon ® and Sinvaqua ® series of inks. Temperatures during ink cure were kept below 150° F. so as not to induce shrinkage of film 21 and application tape 22; the stiffness and high basis weight of the sheet material allowed for easy handling and transfer of the sheets during printing.

Transfer tape 40: a substrate 41 of kraft glassine paper differentially coated on its two surfaces with silicone release agents (Daubert 2-65KGF-147). The substrate was 0.0034" thick with a basis weight of 62 pounds/-ream, and had a Mullen Burst strength of 45 psi minimum, Elmendorf tear values of 40 minimum (MD and XD), tensile strength at break (MD, 20 mm/minute crosshead speed) of 23.5 kg/inch width at 2% elongation and a tensile strength at break (XDD, 50 mm/minute crosshead speed) of 11 kg/inch width at 5.5% elongation. The Kiel release value was 5 g/inch width for one surface of the substrate 41 and 12 g/inch width for the other surface. An acrylic adhesive (Duro-Tak 80-1047 from National Starchy and Chemical) cross-linked with 0.025% (solids on solids) of a melamine formaldehyde resin (Uformite MM-55 #27-8903) was applied to the surface of the substrate with the 12 g/inch width Kiel release value at a coating weight of 17 pounds/ream to provide a 0.001" thick layer of transfer adhesive 42.

After surface 33 of the polyvinyl fluoride film 21 of this Example 1 was printed with signs as described above, the foregoing transfer tape 40 was laminated over printed surface 33 with its adhesive 42 in contact with surface 33. The adhesion of the layer of transfer adhesive 42 to printed surface 33 was greater than 40 ounces/inch width. The polyken probe tack of the adhesive 42 was measured at 300 g/cm nominal after lamination to surface 33. Lamination of transfer tape 40 to printed sheet material 20' proved to be very straightforward and required less manipulation than lamination of prior art paper application tapes to the prior art vinyl films used for outdoor signs.

Following joinder of the transfer adhesive 42 over the printed surface 33 of the polyvinyl fluoride film 21 of the above sheet material 20', the composite assembly was field tested by an applicator company on a trailer body made of corrugated and riveted painted aluminum. The applicator first removed carrier tape 23, which presented no significant problems since adhesive layer 29 of the carrier tape was releasably adhered to surface 27 of the substrate of the application tape 22. The applicator next removed substrate 41 of transfer tape 40 from the assembly, which resulted in the layer of transfer adhesive 42 remaining bonded over printed surface 33 of film 21. The printed signs were then applied onto the trailer body and adhered to the trailer body by means of adhesive 42; the assembly at this point in the application process included adhesive 42, printed film 21 and application tape 22, and it was found that this assembly handled extremely well during application. The tack of the adhesive 42 was low enough to allow repositionability of the sign on the trailer body, which was squeegeed in place after being properly located. It was found that the printed reference lines 51 and 52 on the transparent application tape assisted in properly locating the sign on the trailer body. After the sign was squeegeed in place, the bond of adhesive 42 to the trailer body was sufficiently strong to prevent disturbance of the sign during removal of the application tape. Of interest, it was also noted during the field testing that the low tack of adhesive 42 and the relatively high tensile strength of the polyvinyl fluoride plastic film 21 allowed an applicator to recover as useable a sign that was folded upon itself, adhesive against adhesive; this is an advantage of the sheet material constructions of the present invention which is not attainable with the prior art vinyl films described previously in this specification. The application of the printed sheet material 20' was accomplished by the applicator using the traditional tools in their usual fashion. Other field testing demonstrated that the printed sheet material 20' handled extremely well on various difficult installation surfaces, and that the adhesive 42 of this Example 1 adheres very well to Tedlar® clad fiberglass panels, which also are often used for trailer bodies. In all respects, the field testing of the sheet material 20' of Example 1 demonstrated that it provides significant and important benefits to both a printing company and an applicator company, in addition to providing the end user with attractive, durable outdoor signage. The sheet material of this Example is considered to be the best mode for practice of our invention at the filing date of this patent and is the construction that will be introduced commercially after the filing date.

EXAMPLE 2

Sheet material 20 as described in part 3 above and illustrated in FIGS. 7-15 using the same materials for plastic film 21, application tape 22, carrier tape 23 and transfer tape 40 as described in Example 1 was made except that the substrate 24 of the application tape was 0.003" thick medium density polyethylene and did not include printed reference lines 51 and 52. Test signs were printed on the exterior surface 33 of the polyvinyl fluoride film 21 of sheet material 20 in the same manner as described in Example 1, and the printed signs were applied to a trailer body of corrugated and riveted painted aluminum in the manner described in Example 1.

It was found that sheet material 20 of this Example 2 behaved in the same manner as the sheet material 20' of Example 1 during both printing operations and lamination of transfer tape 40 to the sheet material. Application was also readily accomplished with the traditional tools used for applying signs of this type, and the transparent substrate and adhesive of the application tape assisted in accurately locating the sign on the panels.

EXAMPLE 3

Sheet material 20 according to the embodiment of the present invention described in part 5 above was made with the same materials for plastic film 21, carrier tape 23 and transfer tape 40 as set out in Example 1. However, the application tape 22 consisted of a 43 pound-/ream rubber fibrous paper, 0.0042 inches thick coated with 17 pound/ream (0.001 inches thick) rubber base adhesive a adhesive layer 25. This material is available commercially from American Bilt Rite as their product #6760. The machine direction tensile strengths at break of the application tape were 11 kg/inch width at 3% elongation at 30° F., 4.1 kg/inch width at 2% elongation at 75° F. and 2.7 kg/inch width at 1.3% elongation at 110° F. The cross machine direction tensile strengths of the application tape when elongated to 5% were 4.5 kg/inch width at 30° F., 2 kg/inch width at 75° F. and 1.5 kg/inch width at 110° F. The adhesion of the adhesive 25 to the first surface 32 of the polyvinyl fluoride plastic film 21 was measured at 4 ounces/inch of width. The adhesion of the adhesive layer 29 of the carrier tape 23 to the uncoated surface 27 of the application tape was 16 ounces/inch width. Thus, the application tape of this Example was releasably adhered to the film 21 and the carrier tape 23 was releasably adhered to the application tape.

During laboratory trials, printing signs on the exterior surface 33 of plastic film 21 of the sheet material of this Example 3 proved to be satisfactory with operating and performance characteristics similar to the sheet materials of Examples 1 and 2. Transfer tape 40 was joined to the printed sheet material in the same manner and with the same results as reported in Examples 1 and 2. The application of a printed sign to test panels of aluminum and fiberglass also was accomplished with the traditional tools and the sign could be appropriately positioned on the panels even with the nearly opaque substrate of the application tape, although the advantages of a transparent application tape found with the sheet materials of Examples 1 and 2 were not present with the sheet material of this Example 3. However, most applicators are accustomed to applying vinyl signs with paper application tapes, so that the sheet material of this Example should present no additional problems during application.

The new sheet materials described in parts 3, 4 and 5 and the Examples of this specification can be made in the form of sheets or as a web that is wound into a roll. The sheets or webs can be in the size desired for the sign or cut to the appropriate size after a sign has been printed on polyvinyl fluoride film 21. Signs made from the sheet materials can have various shapes. Rectangular and square signs are commonly used. Also, however, the signs can be cut into other shapes such as circular, oval, triangular, etc., as may be required by the end user, by contour cutting by either of two methods. One method is to cut transfer tape 40, film 21 and application tape 22 in the desired shape, weed out the waste portions of these three layers, and leave the carrier tape uncut. A second method is to cut through all layers of the sheet material and transfer tape, i.e. transfer tape 40, film 21, application tape 22 and carrier tape 23 and separate out the waste portions of these layers. Cutting of the sheet materials typically will be done by the printing company who prints a sign 4 on film 21 of the materials.

The several constructions of sheet materials 20 and 20' described above provide several novel important and useful technical advantages to the end users of printed outdoor signage. As shown in FIGS. 14 and 15 in particular, the graphics of sign 4 when applied to a surface such as the side of trailer 2 are completely covered by the polyvinyl fluoride film 21. Film 21 thereby serves to protect the printed sign graphics from physical damage and vandalism such as graffiti; further, film 21 functions to protect printed sign 4 from fading on exposure to adverse weather conditions and also fading due to ultraviolet rays from sunshine, in addition to which the film protects adhesive 42 from similar environmental damage. The latter function is achieved since the polyvinyl fluoride film can incorporate UV absorbers to provide excellent UV screening properties, which are employed in the construction of sheet materials 20 and 20' to reduce or prevent fading of the printed graphics from exposure to sunlight. Further, a polyvinyl fluoride film 21 resists changes in temperature and humidity, possesses excellent dimensional stability and is not subject to UV degradation. Polyvinyl fluoride films do not dry out or become brittle, so that a film 21 will not chip, crack or peel during its useful life. Another important advantage is that graffiti can be removed from polyvinyl fluid film 21 with solvents since the film is unaffected by mild solvents that can be used to remove graffiti. In addition to the foregoing, the polyvinyl fluoride film 21 is easily maintained as an outdoor printed signage material since most stains can be washed off with detergents or mild solvents. Another significant advantage is that if a printed sign using polyvinyl fluoride film 21 needs to be removed at a future data, such as for changing signal, removal of the film is faster and easier than removal of a vinyl film of the prior art construction 10.

Still another important and useful characteristic of sheet materials 20 and 20' as described above in parts 3 and 4 resides in the use of a transparent plastic film as the substrate and transparent adhesive for application tape 22. This feature of our new sheet materials 20 and 20' enables the applicator to see the printed sign 4 though the application tape while he or she is adhering a film 21 onto a selected surface such as trailer body 2. This facilitates application of a sign with sheet material 20 in that the applicator is better able to properly align the printed graphics relative to the surface on which the sign is being applied.

The foregoing detailed description is made by reference to several specific embodiments of subsurface printable sheet material suitable for outdoor signage according to the present invention as illustrative, not limiting disclosures and it is anticipated that those of ordinary skill in the art will be able to devise modifications to the described embodiments that will remain within the true spirit and scope of the present invention.

We claim:

1. A subsurface printable, laminated sheet material for use in forming a wear-resistant printed laminate, the sheet material comprising:

a carrier tape including a substrate of plastic film or paper having an exposed surface and having an opposite, adhesive-carrying surface, and a low tack adhesive layer on the adhesive-carrying surface of the substrate;

an application tape including a plastic film or paper substrate having a release surface contacting and releasable from the adhesive layer on the carrier tape when the carrier is removed from the application tape and having an opposite, adhesive-carrying surface, and a low tack adhesive layer on the adhesive carrying surface;

a layer of polyvinyl fluoride film having a release surface contacting and releasable from the adhesive layer on the application tape when the application tape is removed from the layer of polyvinyl fluoride film;

wherein the adhesive on the adhesive-carrying surface of the application tape is releasably adhered to the release surface of the polyvinyl fluoride film and wherein the adhesive layer on the adhesive-carrying surface of the carrier tape is releasably adhered to the release surface of the application tape, and wherein the polyvinyl fluoride film has a printable subsurface opposite its release surface for printing with graphics or reverse image printing with text, and adherence to a supporting surface.

2. A sheet material according to claim 1, further comprising printed graphics or reverse image printed text on the subsurface of the polyvinyl fluoride film; and further comprising a layer of pressure-sensitive adhesive covering the printed graphics o text to adhere the sheet material to the supporting surface.

3. A sheet material according to claim 2, further comprising:

a release liner releasably adhered to the pressure-sensitive adhesive covering the printed graphics or text, the release liner covering the adhesive to prevent adhesion of the sheet material to other materials during transportation and handling prior to installation on the supporting surface.

4. A sheet material according to claim 1, wherein:

the substrate of the application tape is transparent; and wherein the adhesive on the adhesive-carrying surface of the transparent substrate is a transparent pressure-sensitive adhesive.

5. A sheet material according to claim 1, wherein:

the substrate of the application tape is opaque.

6. A sheet material according to claim 1, wherein: the substrate of the application tape includes printed reference lines aiding alignment of text or graphics printed on the subsurface of the polyvinyl fluoride film.

7. A sheet material according to any one of claim 1, 2, 3, 4, 5, or 6 wherein: the substrate of the application tape includes printed reference lines comprising a first set of spaced parallel lines and a second set of spaced parallel lines transverse to said first set of spaced parallel lines.

8. A sheet material according to claim 1, wherein: the polyvinyl fluoride film is about 1 to 5 mils thick.

9. A sheet material according to claims 1 or 4, wherein: the substrate of the application tape is a plastic film of rubber modified high density polyethylene or polypropylene.

10. A sheet material according to claim 1, wherein: the substrate of the carrier tape is paper with a basis weight in the range from 90 to 150 pounds per ream; and wherein the adhesive-carrying surface of the carrier tape substrate is coated with low density polyethylene; and wherein the exposed surface of the carrier tape substrate is coated with high density polyethylene.

11. A sheet material according to claim 1, wherein: the substrate of the carrier tape is about 5 to 10 mils thick and is a high density polyethylene film, a polyester film or a polystyrene film.

12. A sheet material according to any one of the claims 1, 2, 4, 5, or 6, wherein: the adhesive layer on the application tape has an adhesion to the release surface of the polyvinyl fluoride film in a range from 3 to 20 ounces/inch of width.

13. A sheet material according to any one of the claims 1, 2, 3, 4, 5 or 6, wherein: the polyvinyl fluoride film includes one or more ultraviolet light absorbing or screening compounds.

* * * * *

UNITED STATES PATENT AND TRADEMARK OFFICE
CERTIFICATE OF CORRECTION

PATENT NO. : 5,225,260

DATED : July 6, 1993

INVENTOR(S) : McNaul, et al.

It is certified that error appears in the above-identified patent and that said Letters Patent is hereby corrected as shown below:

| | |
|---|---|
| Col. 12, line 59 | "Daubert 2-65KGF-147" should read --Daubert 2-65KG-157--. |
| Col. 12, line 65 | "XDD" should read --XD--. |
| Col. 13, line 2 | "National Starche" should read --National Starch--. |
| Col. 13, line 4 | "8903" should read --803--. |
| Col. 14, line 38 | "a" should read --as--. |
| Col. 15, line 53 | "fluid" should read --flouride--. |
| Col. 15, line 61 | "data" should read --date--. |
| Col. 15, line 61 | "signal" should read --signs--. |
| Col. 16, line 12 | After "limiting" insert --,--. |
| Col. 16, line 28 | "carrier" should read --carrier tape--. |
| Col. 16, line 32 | "adhesive carrying" should read --adhesive-carrying--. |

UNITED STATES PATENT AND TRADEMARK OFFICE
CERTIFICATE OF CORRECTION

PATENT NO. : 5,225,260 Page 2 of 2

DATED : July 6, 1993

INVENTOR(S) : McNaul, et al.

It is certified that error appears in the above-identified patent and that said Letters Patent is hereby corrected as shown below:

Col. 16, line 39 After "film" insert --,--.

Col. 16, line 43 "," should read --;--.

Col. 16, line 52 "o" should read --or--.

Signed and Sealed this

First Day of March, 1994

Attest:

BRUCE LEHMAN

*Attesting Officer* *Commissioner of Patents and Trademarks*